United States Patent
Kim et al.

(10) Patent No.: US 9,034,254 B2
(45) Date of Patent: May 19, 2015

(54) TITANIUM OXIDE IMMOBILIZED WITH BIORECEPTORS AND ANTIBACTERIAL METHOD USING THE SAME

(71) Applicant: KOREA INSTITUTE OF SCIENCE AND TECHNOLOGY, Seoul (KR)

(72) Inventors: Byoung Chan Kim, Seoul (KR); Jong Soo Jurng, Seoul (KR); Min Young Song, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 129 days.

(21) Appl. No.: 13/672,399

(22) Filed: Nov. 8, 2012

(65) Prior Publication Data
US 2013/0280125 A1    Oct. 24, 2013

(30) Foreign Application Priority Data

Apr. 19, 2012 (KR) .......................... 10-2012-0041085

(51) Int. Cl.
| | |
|---|---|
| *A61L 2/00* | (2006.01) |
| *C09K 3/00* | (2006.01) |
| *A61L 9/00* | (2006.01) |
| *G01N 33/53* | (2006.01) |
| *A61L 2/10* | (2006.01) |
| *A61L 2/08* | (2006.01) |

(52) U.S. Cl.
CPC .. *A61L 2/10* (2013.01); *A61L 2/088* (2013.01)

(58) Field of Classification Search
CPC ............... A61L 2/00; A61L 9/00; A61L 9/20; A61L 9/205; A61K 8/29; A61K 8/64; A61K 8/66; A61K 8/606

USPC ......... 422/24, 28; 252/380, 519.12; 424/76.1, 424/1.49; 435/7.8, 173.1, 267

See application file for complete search history.

(56) References Cited

U.S. PATENT DOCUMENTS

| | | |
|---|---|---|
| 5,366,746 A | 11/1994 | Mendenhall |
| 6,086,936 A | 7/2000 | Wilson et al. |
| 6,387,844 B1 | 5/2002 | Fujishima et al. |
| 6,583,176 B2 | 6/2003 | Arata |
| 6,777,357 B2 | 8/2004 | Aso et al. |

(Continued)

OTHER PUBLICATIONS

Selective Killing of a Single Cancerous T24 Cell with $TiO_2$ Semiconducting Microelectrode under Irradiation, Hideki Sakai et al., Department of Applied Chemistry, Faculty of Engineering, The University of Tokyo, Hongo 7-3-1, Bunkyo-ku, Tokyo 113, School of Medicine, Yokohama City University, Fukuura, Kanazawa-ku, Yokohama 236, Chemistry Letters 1995, pp. 185-186.

(Continued)

*Primary Examiner* — Monzer R Chorbaji
(74) *Attorney, Agent, or Firm* — NSIP Law

(57) ABSTRACT

Disclosed is an antibacterial composition comprising titanium oxide particles immobilized with an antibody having affinity and cognitive power to a microorganism of interest, and a method for sterilizing the microorganism by using the same. In particular, the present invention relates to a method for preparing functional titanium oxide particles capable of recognizing a microorganism or a virus of interest, and a method for selectively and efficiently sterilizing the same by using the functional titanium oxide particles, and not for randomly sterilizing microorganisms or viruses by using conventional titanium oxide particles having no recognition power to a microorganism or a virus of interest.

11 Claims, 4 Drawing Sheets

(56) References Cited

U.S. PATENT DOCUMENTS

| | | |
|---|---|---|
| 6,780,332 B2 | 8/2004 | Shiau et al. |
| 7,396,459 B2 | 7/2008 | Thorpe |
| 2004/0062744 A1 | 4/2004 | Miyamoto et al. |
| 2007/0207186 A1* | 9/2007 | Scanlon et al. ............... 424/424 |
| 2010/0261244 A1 | 10/2010 | Kim et al. |

OTHER PUBLICATIONS

Matsui, Kazusa et al. "Biofunctional TiO2 nanoparticle-mediated photokilling of cancer cells using UV irradiation." *MedChemComm* 1.3 (2010): 209-211.

* cited by examiner

US 9,034,254 B2

TITANIUM OXIDE IMMOBILIZED WITH BIORECEPTORS AND ANTIBACTERIAL METHOD USING THE SAME

CROSS-REFERENCE TO RELATED APPLICATION

This application claims under 35 U.S.C. §119(a) the benefit of Korean Patent Application No. 10-2012-0041085 filed Apr. 19, 2012, the entire contents of which are incorporated herein by reference.

FIELD OF THE INVENTION

The present invention relates to an antibacterial composition comprising titanium oxide immobilized with an antibody having affinity and cognitive power to a microorganism of interest, and a method for sterilizing the microorganism by using the same. In particular, the present invention relates to a method for preparing functional titanium oxide particles wherein an antibody capable of recognizing a microorganism or a virus of interest is immobilized on the surface thereof, and a method for selectively and efficiently sterilizing the microorganism or virus of interest by using the functional titanium oxide particles.

BACKGROUND

Generally, various methods such as a filtering method using a filter (U.S. Pat. No. 6,780,332), a high/low temperature treatment method (U.S. Pat. No. 5,366,746; U.S. Pat. No. 6,086,936), an antibiotic treatment method (U.S. patent Ser. No. 10/415,219), a disinfectant method (U.S. Pat. No. 6,583,176) and a UV irradiation method (U.S. Pat. No. 7,396,459) have been widely used in the art for inactivating a microorganism (a bacteria or a virus) or preventing a subject from being infected therewith. Recently, it has been developed a method for sterilizing a microorganism by using superoxide ($O_2^-$)/hydroxyl radical (OH) generated from photoreaction of a photocatalyst such as titanium oxide (U.S. Pat. No. 6,387,844; U.S. Pat. No. 6,777,357). The photocatalyst accelerates a chemical reaction by absorbing light from the outside. Among the photocatalysts, titanium oxide is a stable substance, but under ultraviolet (UV) light, it loses electrons and holes are formed thereon, leading to the excitation into an unstable state. At this time, superoxide ($O_2^-$) or hydroxyl radical (OH) generated from the excitation exerts antibacterial activities by inducing the oxidization or degradation of microorganisms and viruses around. Due to such strong oxidizing power, the attempts for applying titanium oxide to the sterilization by coating the same onto the surface of a support or spreading it in underwater have been remarkably increased. Because said method of coating the support with titanium oxide or dispersing it in an aqueous solution does not have selectivity to a microorganism of interest, the most cases are to merely utilize radicals generated from titanium oxide itself. Further, there is no systemic research on the correlation between the number of microorganisms and the concentration of titanium oxide, and the consideration of UV strength and a period of time being irradiated. For example, in a water system, there are problems in that the residence time of radicals generated from titanium oxide is not last long, and its antibacterial activities is lowered when the distance between the microorganism of interest and the titanium oxide is not extremely close. U.S. patent application Ser. No. 12/743,340 discloses a method for immobilizing titanium oxide particles with a biomolecule, but it provides only the information on sensor application of the immobilized complex and not antibacterial activities thereof.

Sakai et al. reported that a microelectrode comprised of titanium oxide can be used in killing T24 human bladder cancer cells. They also reported that if the microelectrode comprised of titanium oxide is 10 cm or longer distant from the cells, there is no effect of killing the cells. In this research, such poor antibacterial activities are because that direct oxidation is not actively occurred on the surface of the cells due to a very short life span of radicals generated from titanium dioxide (Sakai et al., Chemistry Letter, 1995, 185). In case of using the titanium oxide particles having no selectivity, there is a possibility of sterilizing normal useful microorganisms as well as target microorganisms being sterilized. Further, as suggested in the previous research, because the radicals generated by UV irradiation cannot be delivered to the microorganism, there is a disadvantage in that its antibacterial activity is not strong. The study for utilizing titanium oxide as an antibacterial composition has been actively pursued and relating products have been manufactured. But, there is no report on the development of titanium oxide photocatalytic particles having selectivity to a microorganism of interest as disclosed in the present invention.

SUMMARY OF THE INVENTION

The present inventors have therefore endeavored to overcome the above problems in the art, and developed a method for preparing titanium oxide photocatalytic particles by immobilizing titanium oxide having no selectivity to a microorganism of interest with an antibody capable of recognizing the microorganism. Because the titanium oxide photocatalytic particles of the present invention can selectively bind to the microorganism of interest and generate radicals at the position which is closest thereto, it is possible to effectively show antibacterial activities and thus sterilize the microorganism. Therefore, the present invention is characterized by providing a method for sterilizing a microorganism of interest by using the titanium oxide immobilized with an antibody.

Other objects and advantages of the present invention will be apparent upon consideration of the following specification, with reference to the accompanying drawings and claims.

It is an object of the present invention to provide titanium oxide particles immobilized with a bioreceptor capable of specifically binding to a microorganism of interest, in which the bioreceptor is immobilized onto the titanium oxide particle through the binding between a functional group linked to the titanium oxide particle and the functional group of the bioreceptor.

It is another object of the present invention to provide a method for selectively sterilizing a microorganism of interest by using titanium oxide particles immobilized with an anti body specific to the microorganism, comprising the following steps:

(i) bringing into contact the titanium oxide-antibody complex with the microorganism for a period of time; and (ii) sterilizing the titanium oxide-antibody complex by UV irradiation.

According to the method of the present invention, it is possible to selectively sterilize a microorganism of interest depending on the kind of an antibody immobilized on the titanium oxide particles.

The method of immobilizing titanium oxide particles with an antibody is characterized by forming a carboxyl (—COOH) group through the reaction between the titanium oxide particles and polyacrylic acid (PAA), treating the titanium oxide particles to which PAA is linked with EDC (1-ethyl-3-[3-dimethylaminopropyl]carbodiimide hydrochloride) and sulfo-NHS (N-hydroxysulfosuccinimide) so as to induce the binding between the carboxyl group of the titanium oxide particles and an amine (—NH$_2$) group of the antibody, separating thus prepared titanium oxide particles by centrifugation, and immobilizing the antibody onto the titanium oxide particles. Here, the linking method for the immobilization of an antibody onto titanium oxide particles is not limited to that using PAA, EDC or sulfo-NHS.

According to one preferred embodiment, the present invention provides a titanium oxide-*E. coli* specific antibody complex in which an *E. coli* specific polyclonal antibody is immobilized onto the surface of the titanium oxide particle. Further, according to another embodiment, the present invention provides a method for sterilizing *E. coli*, comprising the steps of:

(i) bringing into contact the titanium oxide-antibody complex with *E. coli* by mixing the titanium oxide particle immobilized with the *E. coli* specific antibody with an *E. coli* containing solution, and (ii) exposing the mixture to UV irradiation.

EFFECT OF THE INVENTION

The features and advantages of the present invention are summarized as follows:

(i) the titanium oxide-bioreceptor particle of the present invention can exhibit excellent antibacterial activity by generating oxidized free radicals under the condition that a microorganism of interest is close to the titanium oxide particle through cross-linkage between a functional group linked to titanium oxide and a functional group of the bioreceptor, and (ii) the titanium oxide-bioreceptor particle of the present invention can more effectively sterilize a microorganism of interest in a smaller amount for a shorter period of time than conventional titanium oxide particles being not immobilized with a microorganism specific antibody.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

DETAILED DESCRIPTION OF THE INVENTION

Figure 1:
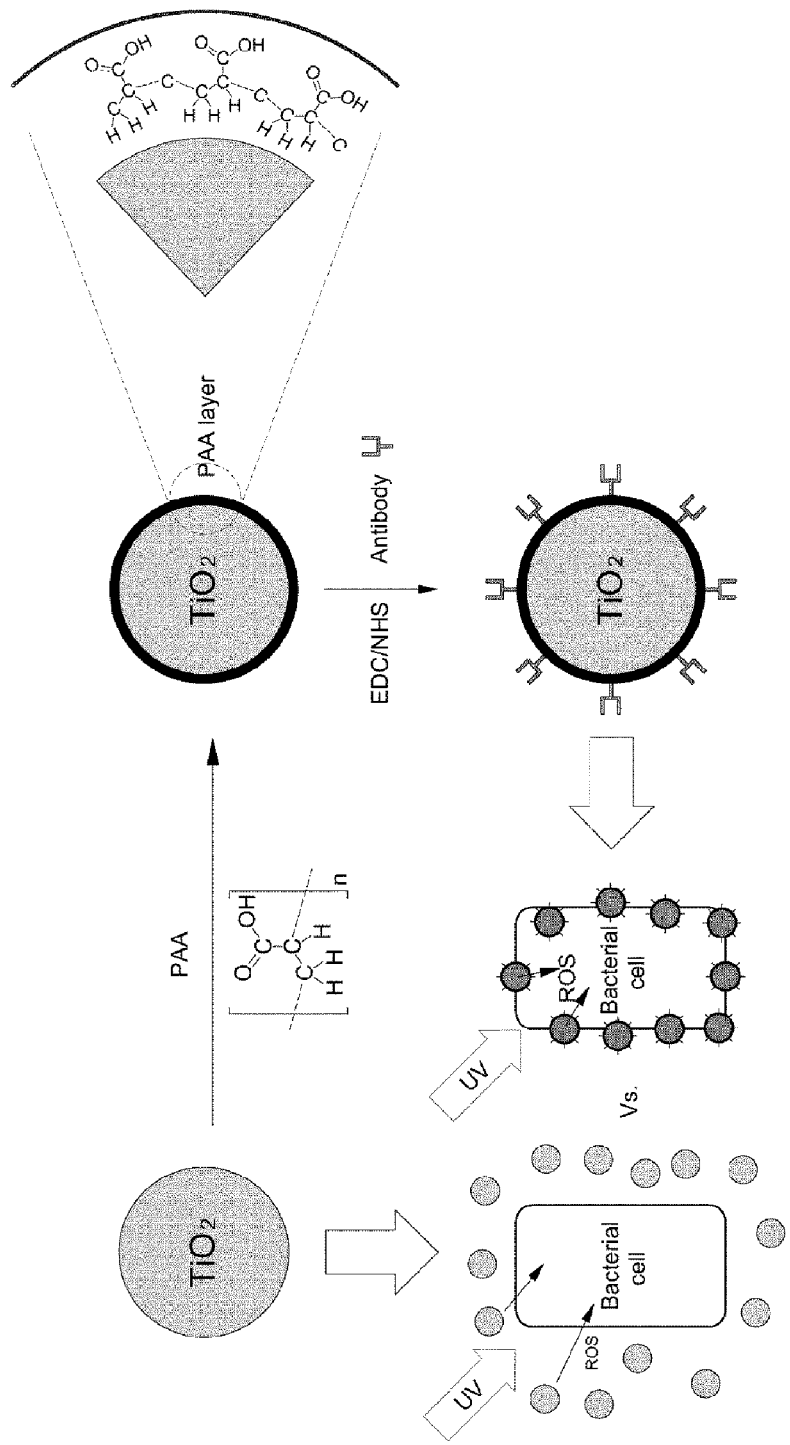
FIG. 1 is a schematic diagram illustrating the method of immobilizing a microorganism specific antibody to titanium oxide particles according to the present invention, in which the principle of enhancing antibacterial activities of the titanium oxide particle immobilized with the antibody is illustrated.

Hereinafter, the present invention will be described in more detail.

According to one aspect of the present invention, it is provided a titanium oxide particle immobilized with a bioreceptor in which the bioreceptor is capable of specifically binding to a microorganism of interest through the binding between a functional group linked to the titanium oxide particle and a functional group of the bioreceptor.

According to a preferred embodiment of the present invention, the binding between a functional group of the titanium oxide particle and a functional group of the bioreceptor is achieved by a cross-linkage between a carbonyl group and an amine group. Especially, it is preferable to be a cross-linkage between a carboxylic acid and an amine group. In particular, an amide linkage, a sulfhydryl-amine linkage, a hydrogen-amine linkage, an amine-amine linkage and a carbonyl-sulfhydryl linkage can be used in the method of the present invention.

In the following Table 1, specific examples of the sulfhydryl-amine linkage, hydrogen-amine linkage, amine-amine linkage and carbonyl-sulfhydryl linkage besides the amide linkage are described.

TABLE 1

Possible linkage between titanium oxide particles and bioreceptors

| Linkage | Reaction scheme |
|---|---|
| Sulfhydryl-Amine | N-succinimidyl-3-(2-pyridyldithio)propionate, SPDP (SPDP reacts with primary amine R—NH₂ to release NHS and form SPDP Activated intermediate; then reacts with sulfhydryl containing compound HS—R' to release Pyridine-2-thione and form Cross-linked Molecules) |
| Hydrogen-Amine | PNP-OTP p-nitrophenyl-2-diazo-3,3,3-trifluoropropionate (reacts with primary amine R—NH₂ to release p-Nitrophenol and form Photoreactive intermediate; U.V. light induces Carbene Formation; reacts with reactive hydrogen containing compound H—R' to form Cross-linked Molecules) |
| Amine-Amine | Cross-linked Molecules |

TABLE 1-continued

Possible linkage between titanium oxide particles and bioreceptors

| Linkage | Reaction scheme |
| --- | --- |
| | 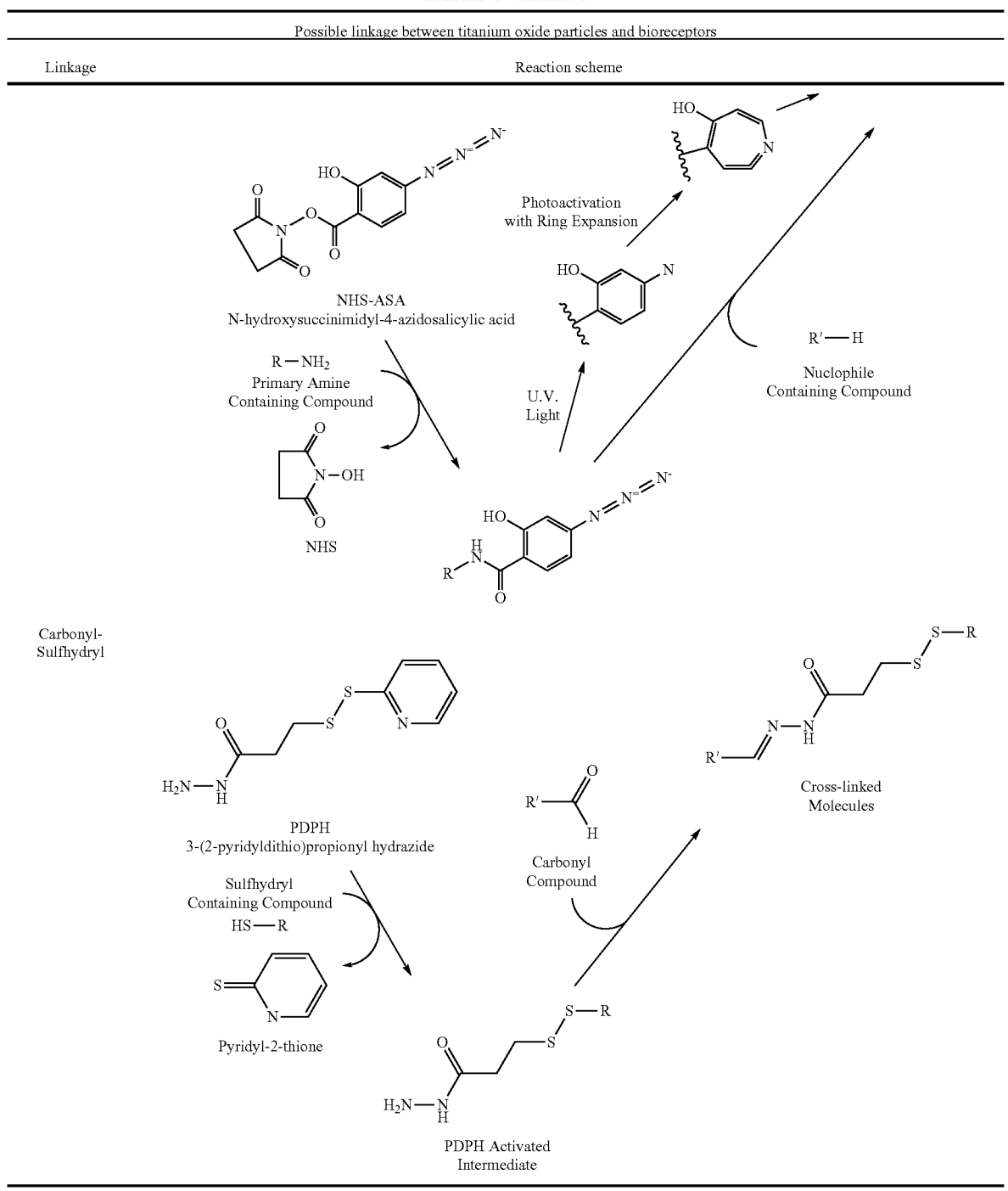 |
| Carbonyl-Sulfhydryl | |

It is preferable to add carbodiimide as a coupling reagent in order to facilitate the direct linkage between a carboxylic acid and an amine, and carbodiimide such as DCC, EDC, DIC and the like can be used.

According to a preferred embodiment of the present invention, the functional group linked to the titanium oxide particle is a carbonyl group, and the functional group linked to the receptor is an amine group.

According to a preferred embodiment of the present invention, the carbonyl group can include acyl chloride, acid anhydride, ester and carboxylic acid, but is not limited thereto. More preferably, the carbonyl group is carboxylic acid.

According to a preferred embodiment of the present invention, the bioreceptor can be one of a protein antibody, DNA as a nucleic acid molecule, and a RNA-based aptamer.

As used herein, the term "nucleic acid molecule" is intended to inclusively mean DNA molecules (gDNA and cDNA) and RNA molecules. Nucleotides are molecules that, when joined, make up the individual structural units of the nucleic acids RNA and DNA, and include analogues having altered sugar or nucleobases as well as naturally occurring nucleotides (Scheit, Nucleotide Analogs, John Wiley, New York (1980); Uhlman and Peyman, Chemical Reviews, 90: 543-584, 1990).

The aptamers are DNA or RNA oligonucleotides that are folded into a certain conformation so as to bind to a target antigen with high specificity and affinity. Such aptamers can be obtained according to a SELEX (Systemic Evolution of Ligands by Exponential Enrichment) method (Tuerk and Gold, Science, 249: 505-510, 1990).

The microorganism specific binding according to the present invention may be applied to all kinds of microorganisms that are being subjected to the binding of the present invention, and thus there is no limitation to the kind of a microorganism.

More preferably, the microorganism specific binding according to the present invention is characterized by showing *E. coli* specific binding.

According to the other aspect, the present invention provides a method of selectively sterilizing a microorganism of interest depending on the type of an antibody immobilized onto the surface of a titanium oxide particle by using the titanium oxide particle immobilized with the antibody, comprising the following steps of:

(i) bringing into contact the titanium oxide-antibody complex with the microorganism for a period of time in order to increase antibacterial effects on the microorganism having a specificity to the antibody by using the titanium oxide particle immobilized with the antibody according to claim 1 or 5; and (ii) sterilizing the microorganism by UV irradiation to the titanium oxide-antibody complex.

According to a preferred embodiment of the present invention, the UV irradiation of step (ii) is carried out for 5 to 15 min, preferably for 10 to 15 min.

FIG. 1 is a schematic diagram illustrating the method of immobilizing a microorganism specific antibody to the titanium oxide particle according to the present invention. The method of immobilizing the antibody to the titanium oxide particles can be carried out by reacting the titanium oxide particle with polyacrylic acid (PAA) to form a carboxylic group (—COOH), treating the titanium oxide particle into which the carboxylic group is introduced with EDC (1-ethyl-3-[3-dimethylaminopropyl]carbodiimide hydrochloride) and sulfo-NHS (N-hydroxysulfosuccinimide), to thereby introduce NHS-ester which is capable of biding to an amine group (—$NH_2$) of the antibody, and immobilizing the antibody thereon. This method is described in detail as follows.

Figure 2:
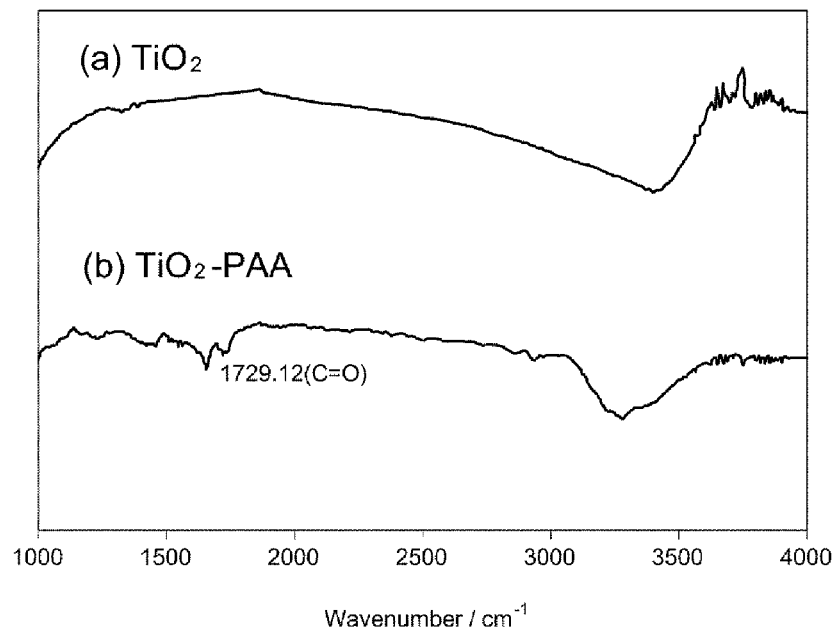
FIG. 2 is the result of analyzing the surface of titanium oxide particles before and after the introduction of a carboxylic group by Fourier transform infrared spectroscopy (FTIR)

First, 0.1 g of the titanium oxide particles are dispersed in 20 mL of a DMF (N,N-dimethylformamide) solution, followed by mixing with 2 mL of a polyacrylic acid solution in dimethylformamide (100 mg PAA/1 mL DMF). The mixed solution obtained above is kept at 150° C. for 5 hrs in a thermostat. After keeping it in the 150° C. thermostat for 5 hr, the mixed solution is cooled down to room temperature and 38 mL of an acetone solution is added thereto. The resulting mixed solution is kept at room temperature for 1 hr. After that, the resulting mixed solution was centrifuged at 4000 rpm for 20 min to separate titanium oxide particles coated with polyacrylic acid. Thus separated titanium oxide particles are washed with 40 mL of ethanol three times, subjected to centrifugation, and dried at room temperature for 24 hr, to thereby the titanium oxide particles coated with polyacrylic acid. The carboxylic group that is introduced into the surface of the titanium oxide particle through the coating of polyacrylic acid can be analyzed by Fourier transform infrared spectroscopy (FTIR). FIG. 2 is the FTIR analysis result of comparing PAA-coated titanium oxide particles and PAA-uncoated titanium oxide particles. The PAA-coated titanium oxide particles show a peak at about 1730 $cm^{-1}$. Such a peak represents the presence of C=O, which suggests that the carboxylic group is successfully introduced into the titanium oxide particles through PAA coating. Thus dried titanium oxide particles are dissolved in a MES buffer (2-[morpholino]ethanesulfonic acid buffer, pH 5.9) to adjust its concentration to 25 mg/mL. To 2 mL of the MES buffer in which the titanium oxide particles are dissolved (pH 5.9) was added EDC and sulfo-NHS at a concentration of 80 mM and 20 mM, respectively. After reacting for 1 hr at room temperature, the titanium oxide particles are isolated by centrifuging at 4000 rpm for 20 min, followed by re-dissolving in 1 mL of the MES buffer. To the resulting solution is added 0.2 mg of an *E. coli* polyclonal antibody and kept at 4° C. for 12 hr. After that, 0.5 mL of an ethanolamine solution (0.1 M) is added to the resulting solution to interfere the NHS-ester being not adhered to the antibody. After keeping it at room temperature for 30 min, the resulting solution is kept at 4° C. for 30 min again. Last, the titanium oxide particles immobilized with the *E. coli* specific antibody are washed with a PBS buffer (pH 7.0) three times, followed by dissolving in 1 mL of the PBS buffer (pH 7.0). The antibacterial activity of the titanium oxide particles immobilized with the *E. coli* specific antibody can be proved in the following Examples.

The present invention is further illustrated by the following examples. However, it shall be understood that these examples are only used to specifically set forth the present invention, rather than being understood that they are used to limit the present invention in any form.

Example 1

After *E. coli* was cultured in 100 mL of a LB medium until the $OD_{600}$ reached 0.4, 12 mL of the culture solution was collected therefrom and subjected to centrifuging so as to separate *E. coli*. Thus separated *E. coli* was washed with 12 mL of a PBS buffer (pH 7.0) and dispersed in 5 mL of a PBS buffer (pH 7.0) in a 20 mL glass bottle. Three such samples were prepared in the same way. Titanium oxide particles immobilized with an *E. coli* specific antibody were added to a Bottle 1 and non-immobilized titanium oxide particles were added to a Bottle 2 in each amount of 0.25 mg. There was no added to a Bottle 3. All three bottles were put into a rotator shaking incubator which was set at 25° C., 200 rpm and subjected to shaking culture for 15 min. After 15 min, a 355 nm UV lamp (15 W) was installed at intervals of about 10 cm therefrom, and then UV was irradiated thereto. Before the UV irradiation (0 min) and after UV was irradiated for 15 min and at thirty-minute intervals thereafter, 100 uL of a sample was collected from each bottle. Thus collected sample was diluted by 1000 times, plated onto each of agar plates, and then incubated in a 37° C. thermostat for 17 hr. After the incubation was completed, the number of *E. coli* cells existed in each bottle was determined by counting the number of colonies formed on the agar plate.

Figure 3:
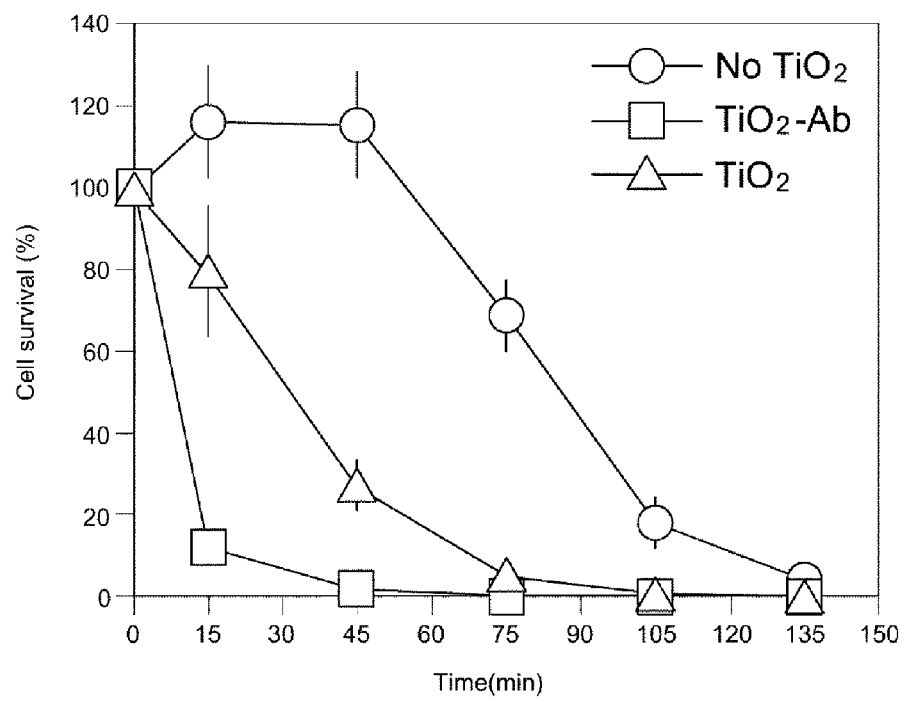
FIG. 3 is the result of comparing the sterilizing effects on *E. coli* after an *E. coli* containing PBS buffer is treated with the titanium oxide particles to which an *E. coli* specific antibody is immobilized or with the titanium oxide particles not being immobilized with the antibody, followed by UV irradiation. As a control, the *E. coli* containing PBS buffer is subjected to only UV irradiation.

The results of measuring the number of *E. coli* cells are shown in FIG. 3 based on the number of *E. coli* cells existed in each bottle at 0 min Generally, under UV irradiation, *E. coli* was killed. At this time, when UV was irradiated in the presence of the titanium oxide particles, titanium oxide generated active oxygen, leading to the increase in antibacterial activity. When compared the death rate of *E. coli* 15 min after the titanium oxide particles were added, in case of adding the titanium oxide particles immobilized with the *E. coli* specific antibody, the death rate of *E. coli* was 90% or higher, and in case of adding the non-immobilized titanium oxide particles, the death rate thereof was only 20%. These results have confirmed that the antibacterial activity of the titanium oxide particles immobilized with the *E. coli* specific antibody was increased by about 4.5-fold. Further, the titanium oxide particles immobilized with the *E. coli* specific antibody shortened the time for completely sterilizing *E. coli* cells by 1 hr. In the case that the titanium oxide particles immobilized with the *E. coli* specific antibody adhered to *E. coli* cells and UV was then irradiated thereto, activated oxygen generated from the titanium oxide particles was delivered more easily to the *E. coli* cells, and thus their antibacterial activity was further enhanced.

This Example is merely illustrative of some methods for assessing the efficiency of the titanium oxide particles immobilized with the *E. coli* specific antibody, and there is no limitation to the methods of culturing *E. coli*, irradiating UV and the like so as to assess its antibacterial activity.

Example 2

It was confirmed in Example 1 that the antibacterial activity of the titanium oxide particles immobilized with the *E. coli* specific antibody was significantly increased. In this Example, whether the titanium oxide immobilized with the *E. coli* specific antibody exhibited antibacterial activity to other cells besides *E. coli* was investigated. For this, *Staphylococcus epidermidis* cells were cultured according to the same method as *E. coli*. As a result of irradiating the cultured *Staphylococcus epidermidis* cells with UV, there was no difference in antibacterial activity between the addition of titanium oxide particles only and that of titanium oxide particles immobilized with the *E. coli* specific antibody (FIG. 3). This was because that the antibody immobilized to the titanium oxide particles was not specific to *Staphylococcus epidermidis*, and thus unlike *E. coli*, the titanium oxide particles did not adhere thereto, which results in dispersing the antibody titanium oxide particles in the culture solution of *Staphylococcus epidermidis*. In case of adding the same amount of the titanium oxide particles, there was no difference in antibacterial activity due to the lack of antibody specificity.

This Example is merely illustrative of some methods for assessing the efficiency of the titanium oxide particles immobilized with the *E. coli* specific antibody, and there is no limitation to the methods of culturing *E. coli*, irradiating UV and the like so as to assess its antibacterial activity.

Example 3

Figure 4:
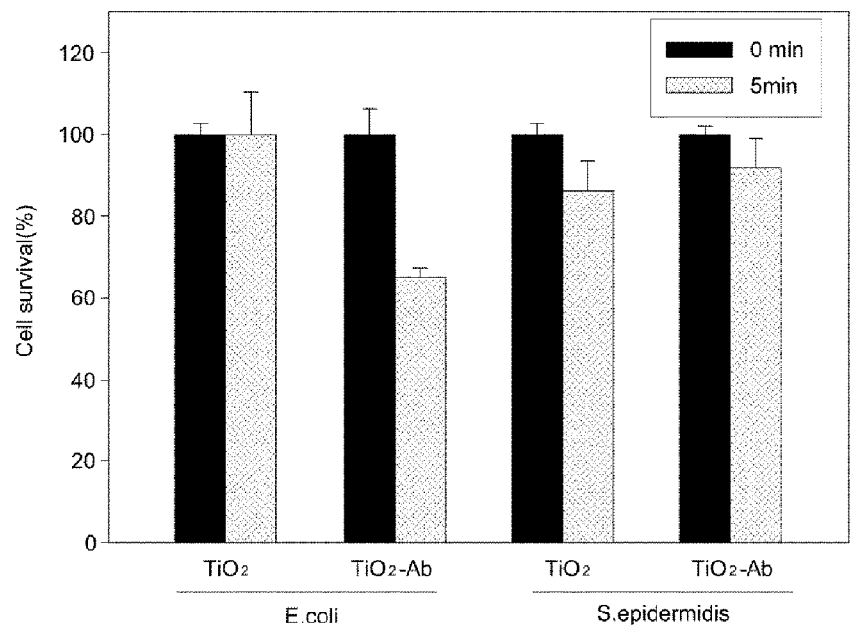
FIG. 4 is the result of comparing the sterilizing effects on *Staphylococcus epidermidis* after a *Staphylococcus epidermidis* containing PBS buffer is treated with the titanium oxide particles to which an *E. coli* specific antibody is immobilized or with the titanium oxide particles not being immobilized with the antibody, followed by UV irradiation.

From Examples 1 and 2, it was found that the titanium oxide particles immobilized with the *E. coli* specific antibody exhibited increased antibacterial activity to *E. coli*. In Examples 1 and 2, two kinds of microorganisms were cultured in a separate cultivator and the antibacterial activities thereon were investigated independently. In order to investigate whether the titanium oxide particles immobilized with the *E. coli* specific antibody can selectively sterilize *E. coli* when two kinds of microorganisms are existed, the antibacterial activity of the titanium oxide particles immobilized with the *E. coli* specific antibody to *E. coli* was measured in the presence of *E. coli* and *Staphylococcus*. After *E. coli* was cultured in 100 mL of a LB medium until the $OD_{600}$ reached 0.4, 12 mL of the culture solution was collected therefrom and subjected to centrifuging so as to separate *E. coli* cells. After *Staphylococcus* was cultured in 100 mL of a LB medium until the $OD_{600}$ reached 0.25, 20 mL of the culture solution was collected therefrom and subjected to centrifuging so as to separate *Staphylococcus* cells. Thus isolated *E. coli* and *Staphylococcus* cells were dispersed in a 25 mL PBS buffer, respectively, and 10 mL of the resulting *E. coli* solution was mixed with 10 mL of the resulting *Staphylococcus* solution. After that, the antibacterial activities to *E. coli* and *Staphylococcus* were measured according to the same method as described in Example 1. At this time, the antibacterial activity was compared 5 min after UV irradiation. As a result, in case of *E. coli*, when the titanium oxide particles immobilized with the *E. coli* specific antibody was added, about 30% of *E. coli* was killed. When the non-immobilized titanium oxide particles were added only, there was no difference in the death rate of *E. coli*. In case of *Staphylococcus*, there was about 10% of difference in the death rate between the addition of the titanium oxide particles immobilized with the *E. coli* specific antibody and the addition of the non-immobilized titanium oxide particles. The same level of death rate was observed irrelevant to the action of the titanium oxide particles immobilized with the *E. coli* specific antibody and the non-immobilized titanium oxide particles. Therefore, it was confirmed that the titanium oxide particles immobilized with the *E. coli* specific antibody selectively acts to only *E. coli* even in the co-presence of *E. coli* and *Staphylococcus*, leading to the increase in antibacterial activity (FIG. 4).

This Example is merely illustrative of some methods for assessing the efficiency of the titanium oxide immobilized with the *E. coli* specific antibody, and there is no limitation to the methods of culturing *E. coli*, irradiating UV and the like so as to assess its antibacterial activity.

What is claimed is:

1. A modified titanium oxide particle, comprising a titanium oxide particle and a bioreceptor immobilized thereon by a functional group linked to the titanium oxide particle, in which the bioreceptor has specific binding affinity to a microorganism of interest through a functional group of the bioreceptor.

2. The modified titanium oxide particle according to claim 1, wherein the immobilization of the bioreceptor is through a linkage selected from the group consisting of a cross-linkage between a carbonyl group and an amine group, a linkage between a sulfhydryl (—SH) group and an amine group, a linkage between an amine group and an amine group, a linkage between hydrogen and an amine group and a linkage between a carbonyl group and a sulfhydryl group.

3. The modified titanium oxide particle according to claim 2, wherein the carbonyl group is acyl chloride, acid anhydride, ester or carboxylic acid.

4. The modified titanium oxide particle according to claim 1, wherein the functional group linked to the titanium oxide particle is a carbonyl group, and the functional group of the bioreceptor is an amine group.

5. The titanium oxide particle according to claim 4, wherein the carbonyl group is acyl chloride, acid anhydride, ester or carboxylic acid.

6. The modified titanium oxide particle according to claim 1, wherein the bioreceptor is a protein antibody, DNA or RNA-based aptamer.

7. The modified titanium oxide particle according to claim 1, wherein the microorganism is *Escherichia coli*.

8. A method of selectively sterilizing a microorganism, comprising the following steps of:
 (i) bringing into contact a titanium oxide-antibody complex with the microorganism, wherein the titanium oxide-antibody complex comprises a titanium oxide particle and an antibody immobilized on the surface of the titanium oxide particle by a functional group linked to the titanium oxide particle, and wherein the antibody has specific binding affinity to the microorganism through a functional group of the antibody; and
 (ii) sterilizing the microorganism by UV irradiation to the titanium oxide-antibody complex.

9. The method according to claim 8, wherein the UV irradiation in step (ii) is carried out for 5 to 15 min.

10. The method according to claim 8, wherein the microorganism of interest in step (i) is *Escherichia coli*.

11. The method according to claim 8, wherein, in step (i), the titanium oxide-antibody complex is brought into contact with a plurality of microorganisms including the microorganism having specific binding affinity to the antibody, and in step (ii), the sterilizing is selective to the microorganism having specific binding affinity to the antibody.

* * * * *